(12) United States Patent
Nolan et al.

(10) Patent No.: US 11,151,785 B2
(45) Date of Patent: Oct. 19, 2021

(54) FINITE ELEMENT MODELING OF ANATOMICAL STRUCTURE (71) Applicant: KONINKLIJKE PHILIPS N.V., Eindhoven (NL)

(72) Inventors: Julian Charles Nolan, Pully (CH); Matthew John Lawrenson, Bussigny-Pres-De-Lausanne (CH); Juergen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/935,731

(22) Filed: Jul. 22, 2020

(65) Prior Publication Data

US 2020/0349762 A1 Nov. 5, 2020

Related U.S. Application Data

(63) Continuation of application No. 15/546,097, filed as application No. PCT/EP2016/051490 on Jan. 26, 2016, now Pat. No. 10,762,701.

(30) Foreign Application Priority Data

Jan. 28, 2015 (EP) .................................. 15152780

(51) Int. Cl.
*G06T 17/20* (2006.01)
*G06T 7/149* (2017.01)
*A61B 5/00* (2006.01)

(52) U.S. Cl.
CPC .............. *G06T 17/20* (2013.01); *G06T 7/149* (2017.01); *A61B 5/7425* (2013.01); *A61B 2576/023* (2013.01)

(58) Field of Classification Search
CPC ... G06T 17/20; G06T 7/149; A61B 2576/023; A61B 5/7425
See application file for complete search history.

(56) References Cited

U.S. PATENT DOCUMENTS 9,607,423 B2 3/2017 Nakagawa
2006/0072821 A1* 4/2006 Wang ....................... G06T 15/08
382/173

(Continued)

OTHER PUBLICATIONS

Cortez et. al., 3D Reconstruction of a Spinal Motion Segment from 2D Medical Images: Objective Quantification of the Geometric Accuracy of the FE Mesh Generation Procedure; Feb. 2013, Portuguese chapter of IEEE EMBS, 3rd Portuguese Meeting in Bioengineering, pp. 1-6 (Year: 2013).*

(Continued)

*Primary Examiner* — Samantha (Yuehan) Wang (57) ABSTRACT

A finite element (FE) model of an anatomical structure is generated based on a fitted model of the anatomical structure and association data. A segmentation model is provided for segmenting the anatomical structure. Association data is obtained which associates a segmentation model part of the segmentation model with a mesh property. The segmentation model part represents a pre-determined anatomical region of interest. The segmentation model is applied to a medical image of a subject, thereby obtaining the fitted model for segmenting the anatomical structure. The finite element model is generated based on the fitted model and the association data, by meshing a finite element model part of the finite element model corresponding with the pre-determined anatomical region of interest in accordance with the mesh property. Advantageously, this results in an efficient generation of the FE model needing fewer manual iterations and/or alterations in the model or in the mesh.

6 Claims, 4 Drawing Sheets

(56) References Cited

U.S. PATENT DOCUMENTS

| | | | |
|---|---|---|---|
| 2006/0078194 A1 | 4/2006 | Fradkin | |
| 2008/0137929 A1* | 6/2008 | Chen | G06T 7/0012 |
| | | | 382/131 |
| 2009/0115796 A1 | 5/2009 | Weese | |
| 2011/0093243 A1* | 4/2011 | Tawhai | G06T 17/20 |
| | | | 703/2 |
| 2014/0324400 A1* | 10/2014 | Quam | G06T 17/20 |
| | | | 703/2 |
| 2015/0294082 A1 | 10/2015 | Passerini | |
| 2016/0242673 A1* | 8/2016 | Grychtol | A61B 5/0809 |
| 2017/0360578 A1 | 12/2017 | Shin | |

OTHER PUBLICATIONS

Pissinelli, et al: "4D Image-based CFD simulation of a compliant blood vessel", International Journal for Numerical Methods in Biomedical Engineering, Mar. 27, 2010, pp. 1-26.

Chopra, P. et al. "TetFusion: an algorithm for rapid tetrahedral mesh simplification," in Proceedings of IEEE Visualization, 2002.

Hansen, K.V. et al., "Region of interest based finite element modelling of the brain an approach to brain surgery simulation", Pattern Recognition, 1998, Proceedings. Fourteenth International Conference on Brisbane, QLD., Australia, Aug. 16-20, 1998, vol. 1, pp. 292-296.

Song, Q. et al: "Cardiac localization in topograms using hierarchical models", 2013 IEEE 10th International Symposium on Biomedical Imaging, Apr. 2013, pp. 105-108.

Bonovas, P.M. et al: "A realistic three dimensional FEM of the human head; 3D FEM of human head", Physiological Measurement, Institute of Physics Publishing, Bristol, GB, vol. 22, No. 1, Feb. 2001, pp. 65-76.

Shigeta, K., et al., "Development of Next Generation Human Fe Model Capable of Organ Injury Prediction", Toyota Motor Corporation, Japan, Paper No. 09-0111, 2009.

Zheng, et al: "Multi-Part Modeling and Segmentation of Left Atrium in C-arm CT for Image-Guided Ablation of Atrial Fibrillation", IEEE Transactions on Medical Imaging, vol. 33, No. 2, Feb. 2014.

Kang, et al: "Heart chambers and whole heart segmentation techniques: review", Journal of Electronic Imaging, 21(1), 010901 (Jan.-Mar. 2012).

Lobos, et al: "Techniques for the generation of 3D Finite Element Meshes of human organs", Informatics in Oral Medicine: Advanced Techniques in Clinical and Diagnostic Technologies, Nov. 19, 2009.

Zhang, et al: "Adaptive and Quality 3d Meshing from Imaging Data", Proceedings of the 8th ACM Symposium on Solid Modeling and Applications, Jun. 16-20, 2003.

* cited by examiner

FINITE ELEMENT MODELING OF ANATOMICAL STRUCTURE

CROSS-REFERENCE TO RELATED APPLICATIONS

This application is a continuation of U.S. application Ser. No. 15/546,097 filed Jul. 25, 2017, now U.S. Pat. No. 10,762,701, issued Sep. 1, 2020, which is the U.S. National Phase application under 35 U.S.C. § 371 of International Application No. PCT/EP2016/051490, filed on Jan. 26, 2016, which claims the benefit of European Patent Application No. 15152780.1, filed on Jan. 28, 2015. These applications are hereby incorporated by reference herein.

FIELD OF THE INVENTION

The invention relates to a system and a method for generating a finite element model of an anatomical structure. The invention further relates to a system and a method for generating association data for use in generating the finite element model of the anatomical structure. The invention further relates to association data for use in generating the finite element model. The invention further relates to a workstation and imaging apparatus comprising the respective system, and to a computer program product comprising instructions for causing processor systems to perform the respective method.

BACKGROUND OF THE INVENTION

Finite Element (FE) methods are numerical methods for approximating solutions of mathematical differential equations governing a domain such as structure. For example, the differential equations may describe a physical or chemical phenomenon in the structure. FE modeling, which is modeling of a structure based on FE methods, may be used to analyze a response of the structure to a change in, for example, a physical state in the structure. An example is the FE modeling of a structure to analyze deformations and mechanical stresses of the structure under a mechanical load. FE modeling may have applications in various fields. For example, in the medical field, FE modeling may be of interest, for a physician to analyze an anatomical structure shown in a 3D image of a patient. Such FE modeling may help the physician, for example, in diagnosis or surgical planning.

In the FE methods which are used in FE modeling, the solution to complex differential equations may be simplified by using an approximation involving a large number of linear equations. This may be similar to an approximation of a circle by a large number of small straight lines. The structure of the problem which may be a line, surface or volume, may be divided into a collection of sub-domains or Finite Elements (for a surface or volume this collection of sub-domains may be referred to as a "mesh") and the global solution for the structure may be calculated by calculating the solution for each of these sub-domains.

A practical consideration of FE methods is that while the accuracy of the solution may increase with the number of the Finite Elements, the computation power and therefore time or expense required to solve the global solution may increase correspondingly. A pragmatic approach may be to have a fine granularity of sub-domains in regions that are of most interest, and a coarser granularity in regions that are of lesser interest. Therefore regions that are key to any problem, or where the mathematical solution changes rapidly, may be calculated with a finer granularity and regions in a periphery with a coarser granularity.

With respect to FE modeling of anatomical structures, current techniques to generate FE models of anatomical structures, often involve multiple iterations and alterations in order to generate an optimal mesh in the FE models in view of the complex characteristics of anatomical structures. Here, the complexity may stem, for example, from complex geometrical characteristics or boundary conditions. In addition, the user may often be required to manually assess the requirements for obtaining a desired mesh in the FE models, which may be prone to mistake and/or lack of accuracy.

SUMMARY OF THE INVENTION

It would be advantageous to obtain an improved system or method for generating a FE model of an anatomical structure with a desired mesh.

To better address this concern, a first aspect of the invention provides a system for generating a finite element model of an anatomical structure based on a fitted model of the anatomical structure and association data, the system comprising:

an input interface configured for receiving:
i) model data defining a segmentation model for segmenting the anatomical structure, the segmentation model representing a reference shape of the anatomical structure, and
ii) association data associating a segmentation model part of the segmentation model with a mesh property, the segmentation model part representing a pre-determined anatomical region of interest;

a segmentation subsystem configured for applying the segmentation model to a medical image of a subject, so as to fit the segmentation model to the anatomical structure in the medical image, thereby obtaining a fitted model providing a segmentation of the anatomical structure, the fitted model comprising a fitted model part providing a segmentation of the pre-determined anatomical region of interest;

a finite element model generating subsystem configured for generating the finite element model based on the fitted model and the association data, said generating comprising meshing a finite element model part of the finite element model in accordance with the mesh property, the finite element model part corresponding with the pre-determined anatomical region of interest. Examples of the mesh property may include mesh resolution or element type.

A further aspect of the invention provides a system for generating association data for use in generating a finite element model of an anatomical structure, the system comprising:

an input interface configured for obtaining model data defining a segmentation model for segmenting the anatomical structure, the segmentation model representing a reference shape of the anatomical structure;

an identifying subsystem configured for identifying a pre-determined anatomical region of interest in the segmentation model, the pre-determined anatomical region of interest having been pre-determined based on a mesh property being desired in meshing a finite element model part of the finite element model which corresponds with the pre-determined anatomical region of interest;

an association subsystem configured for generating association data associating a segmentation model part of the segmentation model with the mesh property, the segmentation model part representing the pre-determined anatomical region of interest.

The above measures involve receiving model data defining a segmentation model for segmenting an anatomical structure, with the segmentation model representing a reference shape of the anatomical structure. The segmentation model may have been generated based on an average of the shape of the anatomical structure over several individuals using, e.g., statistical shape analysis methods. However, the segmentation model may also have been obtained using other methods and from other sources, e.g., medical atlas data. An example of a segmentation model is a surfaced-based model such as mesh model. Another example is volumetric patient model as used in atlas-based segmentation.

The above measures further involve an identifying subsystem configured for identifying a pre-determined anatomical region of interest in the segmentation model, the pre-determined anatomical region of interest having been pre-determined based on a mesh property being desired in meshing a finite element model part of the finite element model which corresponds with the pre-determined anatomical region of interest. Identification of the pre-determined region of interest may be performed based on, for example, geometrical coordinates, anatomical characteristics or other distinctive characteristics of the pre-determined region of interest. The identification subsystem may, for example, use a pre-generated list or look-up table, which identifies characteristics of the pre-determined region of interest. The mesh property may be selected based on meshing requirements of the finite element model part of the finite element model. For example, previous simulations may have provided information on a required mesh resolution in a particular part.

Furthermore, an association subsystem configured for generating association data associating a segmentation model part of the segmentation model which represents the pre-determined anatomical region of interest with the mesh property. For example, in case the model data comprises labels identifying different segmentation model parts of the segmentation model, the association data may comprise or refer to a label which corresponds to the segmentation model part which represents the pre-determined anatomical region of interest, thereby associating the mesh property to said segmentation model part.

A segmentation subsystem is provided for applying the segmentation model to a medical image of a subject, so as to fit the segmentation model to the anatomical structure in the medical image, thereby obtaining a fitted model providing a segmentation of the anatomical structure, the fitted model comprising a fitted model part providing a segmentation of the pre-determined anatomical region of interest For example, the segmentation model may be a deformable model and the fitted model may be obtained by applying the deformable model to the medical image of the subject. Another example is that in case the segmentation model is a volumetric patient model, the model may be morphed to the medical image using non-rigid registration.

It is noted that, when applying the segmentation model to the medical image of the subject, the segmentation model part of the segmentation model may be fitted to a corresponding anatomical region of interest in the medical image, e.g., representing a same or similar anatomical region. As such, by fitting the segmentation model to the medical image, the anatomical region of interest in the medical image may be identified. It is further noted that, by associating the mesh property to the segmentation model part of the segmentation model, the association data may implicitly or inherently also associate the mesh property to the fitted model part of the fitted model. For example, in case the association data refers to a label identifying the segmentation model part of the segmentation model, the same label may be present in the fitted model. The association data may thus also associate the mesh property with one or both of the segmentation model and the fitted model.

It is noted that the medical image may be, e.g., a volumetric image, or may be constituted by a stack of image slices, and may be acquired by various imaging modalities such as Computed Tomography (CT) and Magnetic Resonance Imaging (MRI).

Furthermore, a finite element model generating subsystem is provided for generating the finite element model based on the fitted model and the association data associating a segmentation model part of the segmentation model with a mesh property, the segmentation model part representing a pre-determined anatomical region of interest. Here, the generating comprises meshing a finite element model part of the finite element model which corresponds with the pre-determined anatomical region of interest. It is noted that the finite element model part of the finite element model corresponds to the pre-determined anatomical region of interest, in that it may represent a same or similar anatomical region. The mesh property may, for example, define a desired mesh resolution. Based on the desired mesh resolution, finite element model part of the finite element model may be meshed so as to obtain the desired mesh resolution. The finite element model generation subsystem may be based on known techniques such as those employed in commercial software such as Abaqus or ANSYS. For mesh generation, different known methods may be used, such as methods based on Fortune's algorithm or Ruppert's algorithm.

Here, the term "mesh" is well known in the field of FE modeling, and may refer to a set of nodes connected by lines that cover either an entire surface or entire volume. For a surface mesh, the constituent Finite Elements may also be surfaces, whereas for a volumetric mesh the Finite Elements may also be volumes. The term "Finite Elements" may refer to bounded shapes created by forming the mesh.

With respect to FE modeling of anatomical structures, current techniques involve either manually defining the mesh to be used and therefore using skills of the user to create an appropriate balance of accuracy and computational requirements, or using automated techniques. Techniques involving the manual definition of the FE mesh are typically time consuming and often require multiple iterations, each with a lengthy computational period to test the mesh, in order to arrive at an appropriate solution. Also, as it may be difficult to manually assess the required mesh granularity in order to arrive at an appropriate solution the user may have a tendency to use too-fine mesh in order to 'stay on the safe side'. While this may create an adequate mathematical solution, it may take more processing power, and hence either time or expense, than needed. Currently available automated techniques merely take geometrical aspects such as curvatures into consideration, which may not be of relevance for a problem on hand. Therefore, manual assessments and iterations of the mesh by the user following the available automated techniques is often unavoidable.

Based on the insight of the inventors, FE modeling may be based on a segmentation model, e.g., to indicate location and base shape of the anatomical structure in a medical image. FE modeling may then use the segmentation model as a starting point, e.g., as a base FE mesh, to suitably shape a pre-existing FE mesh, etc. A desired mesh property is frequently related to a particular anatomical region, in that the mesh property may be selected to reflect, e.g., a certain material type of the anatomical region. By associating the mesh property to a corresponding segmentation model part of the segmentation model, the FE modeling may directly, from the segmentation model and the therewith associated mesh property, generate the FE model with a finite element model part which corresponds with the pre-determined anatomical region of interest having the particular mesh property. It is therefore not needed for the user to specify the desired mesh property during the FE modeling as it is already associated with the segmentation model in the segmentation model. Compared to an automatic mesh generation based on mere geometric properties of the FE model, the system(s) enable anatomically specific knowledge to be used in the FE modeling. Aspects of the present invention may advantageously result in an efficient generation of the FE model with fewer iterations and alterations in the model or in the mesh in order to generate an optimal meshing of the FE model. Furthermore, mistakes by the user when altering/correcting the mesh/model may be minimized. In addition, user tendency to use too-fine mesh in order to 'stay on the safe side' may be avoided.

Optionally, the mesh property is selected based on at least one out of: (i) a material type of the pre-determined anatomical region of interest (ii) a medical and/or biological condition at the pre-determined anatomical region of interest (iii) a mechanical boundary condition at the pre-determined anatomical region of interest (iv) an anatomical shape of the pre-determined anatomical region of interest. For example, when modeling a cavity, a higher mesh resolution may be used at the wall for computational fluid dynamic (CFD) simulations. In another example, in fluid-solid interaction (FSI) simulations, used, e.g., for blood flow simulations in a cavity, solid part and fluid part may share vertices and mesh topology at the solid-fluid boundary. Such selection of the mesh property based on different simulation conditions may advantageously allow taking various prior knowledge/information into account when generating the finite element model.

Optionally, the mesh property is one out of: (i) mesh resolution and (ii) element type. Mesh resolution is of particular relevance in FE modeling, but also element type is of relevance. Examples of element type include linear and quadratic tetrahedra, hexahedra or membrane elements. This may advantageously allow obtaining an optimal balance between robustness and computational expense of a simulation. For example, quadratic hexahedral elements may be very robust, but computationally expensive and therefore, these types of element may be selected in particular regions in an FE model based on an anatomically specific knowledge.

Optionally, the segmentation model is a mesh model, thereby obtaining as fitted model a mesh model and the finite element model generating subsystem is configured for generating the finite element model by further meshing the fitted mesh model based on the association data. The fitted model may thus be used as base mesh for the subsequent FE modeling. Mesh modification methods such as mesh pillowing node set repositioning or mesh deformation may be used to obtain the desired mesh property at the finite element model part of the finite element model.

Optionally, the segmentation model is a shape model. The shape model may thus be used as base geometrical model for the subsequent FE modeling. The shape model may be obtained using statistical shape modeling method as a robust tool for segmentation of anatomical structures.

Optionally, the association data is generated as metadata for the model data, or is encoded in the model data. By encoding the association data in the model data, the association data is explicitly coupled with the model data. Any transmittal, storage, etc., of the model data thus also results in the association data being transmitted, stored, etc.

Optionally, (i) the model data comprises labels identifying different anatomical regions of the segmentation model, and (ii) the association data is generated to comprise or refer to a label corresponding to the pre-determined anatomical region of interest. Anatomical regions are frequently labeled within the model data. Such labeling may be used in the identification and meshing of the anatomical region of interest based on the corresponding label.

Optionally, the segmentation model is a heart model. This may allow FE modeling of the heart, being an example of a complex anatomical structure. In this case, the region of interests may be, e.g., left ventricle, right ventricle, left atrium or the right atrium. Heart analysis using the proposed methods and systems may help a physician, for example, in a diagnostic strategy of a heart disease or a surgical strategy for heart repair.

A further aspect of the invention provides a workstation or imaging apparatus comprising one or both of the systems described above.

A further aspect of the invention provides association data for use in generating a finite element model of an anatomical structure, the association data associating a segmentation model part of a segmentation model with a mesh property, the segmentation model part representing a pre-determined anatomical region of interest, the segmentation model representing a reference shape of the anatomical structure, the mesh property being desired in meshing a finite element model part of the finite element model which corresponds with the pre-determined anatomical region of interest.

Optionally, model data defines a segmentation model for segmenting an anatomical structure, the segmentation model representing a reference shape of the anatomical structure, the model data comprising the association data. The association data may thus be encoded in the model data, e.g., in a header or as one or more properties assigned to the pre-determined region of interest.

A further aspect of the invention provides a method for generating a finite element model of an anatomical structure based on a fitted model of the anatomical structure and association data, the method comprising:
receiving:
i) model data defining a segmentation model for segmenting the anatomical structure, the segmentation model representing a reference shape of the anatomical structure, and
ii) association data associating a segmentation model part of the segmentation model with a mesh property, the segmentation model part representing a pre-determined anatomical region of interest;
applying the segmentation model to a medical image of a subject, so as to fit the segmentation model to the anatomical structure in the medical image, thereby obtaining a fitted model providing a segmentation of the anatomical structure, the fitted model comprising a fitted model part providing a segmentation of the pre-determined anatomical region of interest;
generating the finite element model based on the fitted model and the association data, said generating comprising meshing a finite element model part of the finite element model in accordance with the mesh property, the finite element model part corresponding with the pre-determined anatomical region of interest.

A further aspect of the invention provides a method for generating association data for use in generating a finite element model of an anatomical structure, the method comprising:

obtaining model data defining a segmentation model for segmenting the anatomical structure, the segmentation model representing a reference shape of the anatomical structure;

identifying a pre-determined anatomical region of interest in the segmentation model, the pre-determined anatomical region of interest having been pre-determined based on a mesh property being desired in meshing a finite element model part of the finite element model which corresponds with the pre-determined anatomical region of interest;

generating association data associating a segmentation model part of the segmentation model with the mesh property, the segmentation model part representing the pre-determined anatomical region of interest.

In a further aspect of the invention, a computer program product is provided comprising instructions for causing a processor system to perform one or both of the methods described above.

It will be appreciated by those skilled in the art that two or more of the above-mentioned embodiments, implementations, and/or aspects of the invention may be combined in any way deemed useful.

Modifications and variations of the imaging apparatus, the workstation, the method, and/or the computer program product, which correspond to the described modifications and variations of the system, can be carried out by a person skilled in the art on the basis of the present description.

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

Figure 1:
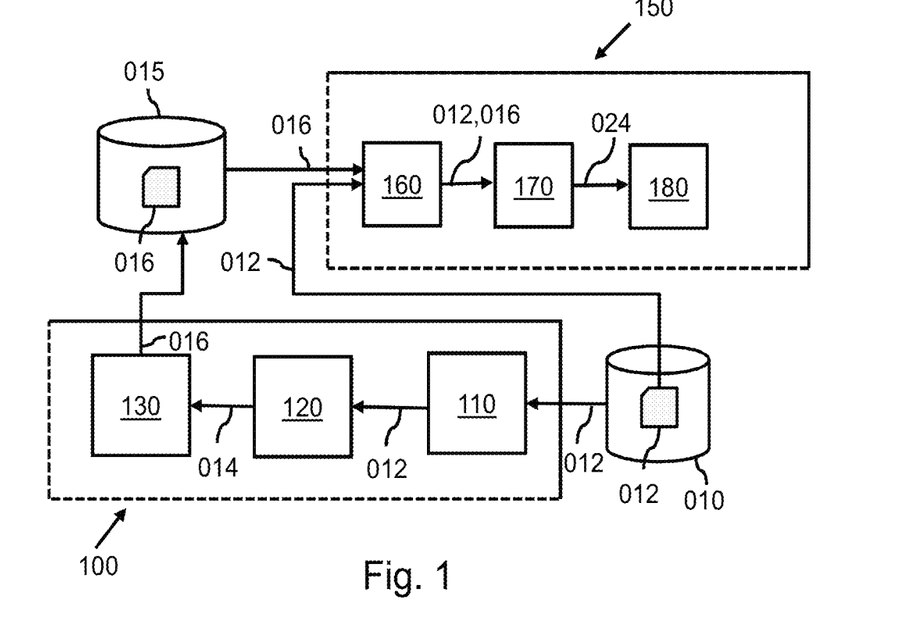
FIG. 1 shows a first system for generating association data for use in generating a finite element model of an anatomical structure, and a second system for generating the finite element model of the anatomical structure based on a fitted model of the anatomical structure and the association data.

FIG. 1 shows a first system 100 for generating association data for use in generating the finite element model of an anatomical structure. FIG. 1 further shows a second system 150 for generating a finite element model of the anatomical structure based on a fitted model of the anatomical structure and association data.

The first system 100 may comprise an input interface 110 configured for obtaining model data 012 defining a segmentation model for segmenting the anatomical structure, the segmentation model representing a reference shape of the anatomical structure. The model data may be obtained for example, from a database 010.

The first system 100 may further comprise an identifying subsystem 120 configured for identifying a pre-determined anatomical region of interest in the segmentation model, the pre-determined anatomical region of interest having been pre-determined based on a mesh property being desired in meshing a finite element model part of the finite element model which corresponds with the pre-determined anatomical region of interest. For that purpose, the identifying subsystem 120 may obtain the model data 012 from the input interface, and output identification data 014 identifying the pre-determined anatomical region of interest in the segmentation model.

The first system 100 may further comprise an association subsystem 130 configured for generating the association data 016 associating a segmentation model part of the segmentation model with the mesh property, the segmentation model part representing a pre-determined anatomical region of interest. For that purpose, the association subsystem 130 may make use of the identification data 014.

The second system 150 may comprise an input interface 160 configured for receiving the model data 012 defining a segmentation model for segmenting the anatomical structure, the segmentation model representing the reference shape of the anatomical structure, and the association data 016 associating a segmentation model part of the segmentation model with a mesh property, the segmentation model part representing a pre-determined anatomical region of interest. The model data 012 and the association data 016 may be received from a same database, or as shown in FIG. 1, from different databases 010, 015. Depending on the form of the database(s) 010, 015, the input interface 160 may take any suitable form, such as an external memory or storage interface, a network interface to local or wide area network, etc. In particularly, the database(s) 010, 015 may be part of a Hospital Information System (HIS) and the input interface 160 may be an interface to the HIS. It is noted that the database(s) 010, 015 may also be internal database(s). Accordingly, the model data 012 and/or the association data 016 may be accessed internally.

The second system 150 may further comprise a segmentation subsystem 170 configured for applying the segmentation model to a medical image of a subject, so as to fit the segmentation model to the anatomical structure in the medical image, thereby obtaining a fitted model providing a segmentation of the anatomical structure, the fitted model comprising a fitted model part providing a segmentation of the pre-determined anatomical region of interest. The segmentation model may have been generated based on an average of the shape of the anatomical structure over several individuals. The segmentation model may have been obtained using other methods and from other sources such as medical atlas data. As shown in FIG. 1, the segmentation subsystem 170 may output the fitted model, e.g., in the form of fitted model data 024.

The second system 150 may further comprise a finite element model generating subsystem 180 configured for generating the finite element model based on the fitted model and the association data 016. For that purpose, the finite element model generating subsystem 180 may receive the fitted model data 024 from the segmentation subsystem 170. In generating the finite element model, the finite element model generating subsystem 180 may then mesh a finite element model part of the finite element model in accordance with the mesh property, the finite element model part corresponding with the pre-determined anatomical region of interest.

It is noted that examples of the mesh property may include mesh resolution or element type. Examples of element type include linear and quadratic tetrahedra, hexahedra or membrane elements.

The segmentation model may have been generated based on an average of the shape of the anatomical structure over several individuals using, e.g., statistical shape analysis methods. However, the segmentation model may also have been obtained using other methods and from other sources, e.g., medical atlas data.

Identification of the pre-determined region of interest may be performed based on, for example, geometrical coordinates, anatomical characteristics or other distinctive characteristics of the pre-determined region of interest in the segmentation model. The identification subsystem may, for example, use a pre-generated list or look-up table, which identifies characteristics of the pre-determined region of interest in the segmentation model. The mesh property may be selected based on mesh property being desired in meshing a finite element model part of the finite element model which corresponds with the pre-determined anatomical region of interest. For example, previous simulations may have provided information on a required mesh resolution in a particular region.

Figure 2:
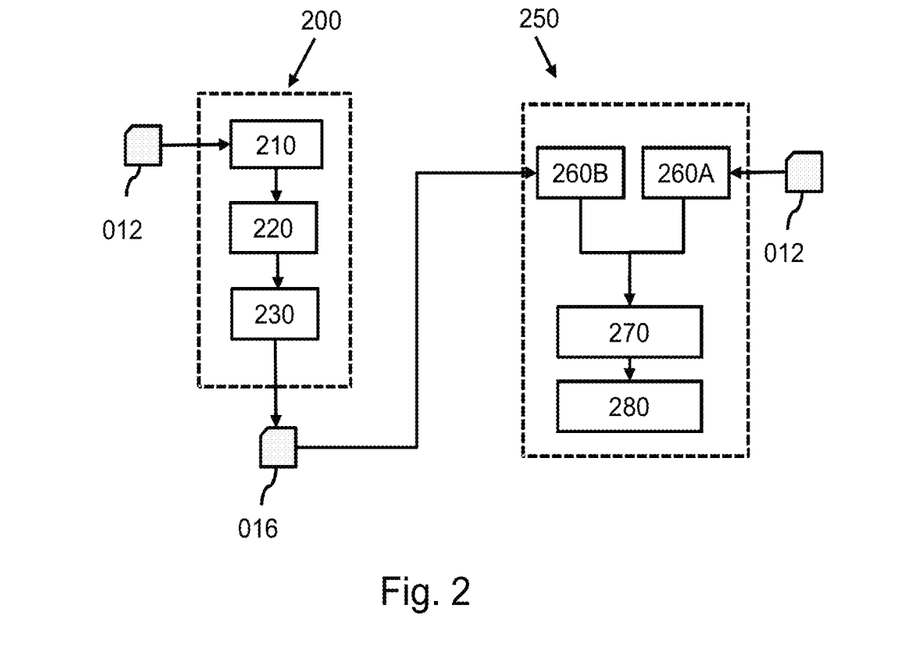
FIG. 2 shows a first method for generating association data for use in generating a finite element model of an anatomical structure, and a second method for generating the finite element model of the anatomical structure based on a fitted model of the anatomical structure and the association data.

FIG. 2 shows a first method 200 for generating the association data 016 for use in generating the finite element model of the anatomical structure. FIG. 2 further shows a second method 250 for generating a finite element model of an anatomical structure based on a fitted model of the anatomical structure and association data 016.

The first method 200 may comprise obtaining 210 the model data 012 defining a segmentation model for segmenting the anatomical structure, the segmentation model representing a reference shape of the anatomical structure.

The first method 200 may further comprise identifying 220 a pre-determined anatomical region of interest in the segmentation model, the pre-determined anatomical region of interest having been pre-determined based on a mesh property being desired in meshing a finite element model part of the finite element model which corresponds with the pre-determined anatomical region of interest.

The first method 200 may further comprise generating 230 the association data 016 associating a segmentation model part of the segmentation model with the mesh property, the segmentation model part representing the pre-determined anatomical region of interest.

The second method 250 may comprise receiving 260A model data 012 defining a segmentation model for segmenting the anatomical structure, the segmentation model representing a reference shape of the anatomical structure. The second method 250 may further comprise receiving 260B association data 016 a segmentation model part of the segmentation model with a mesh property, the segmentation model part representing a pre-determined anatomical region of interest.

The second method 250 may further comprise applying 270 the segmentation model to a medical image of a subject, so as to fit the segmentation model to the anatomical structure in the medical image, thereby obtaining a fitted model providing a segmentation of the anatomical structure, the fitted model comprising a fitted model part providing a segmentation of the pre-determined anatomical region of interest.

The second method 250 may further comprise generating 280 the finite element model based on the fitted model and the association data associating 016, said generating 280 comprising meshing a finite element model part of the finite element model in accordance with the mesh property, the finite element model part corresponding with the pre-determined anatomical region of interest.

Figure 3:
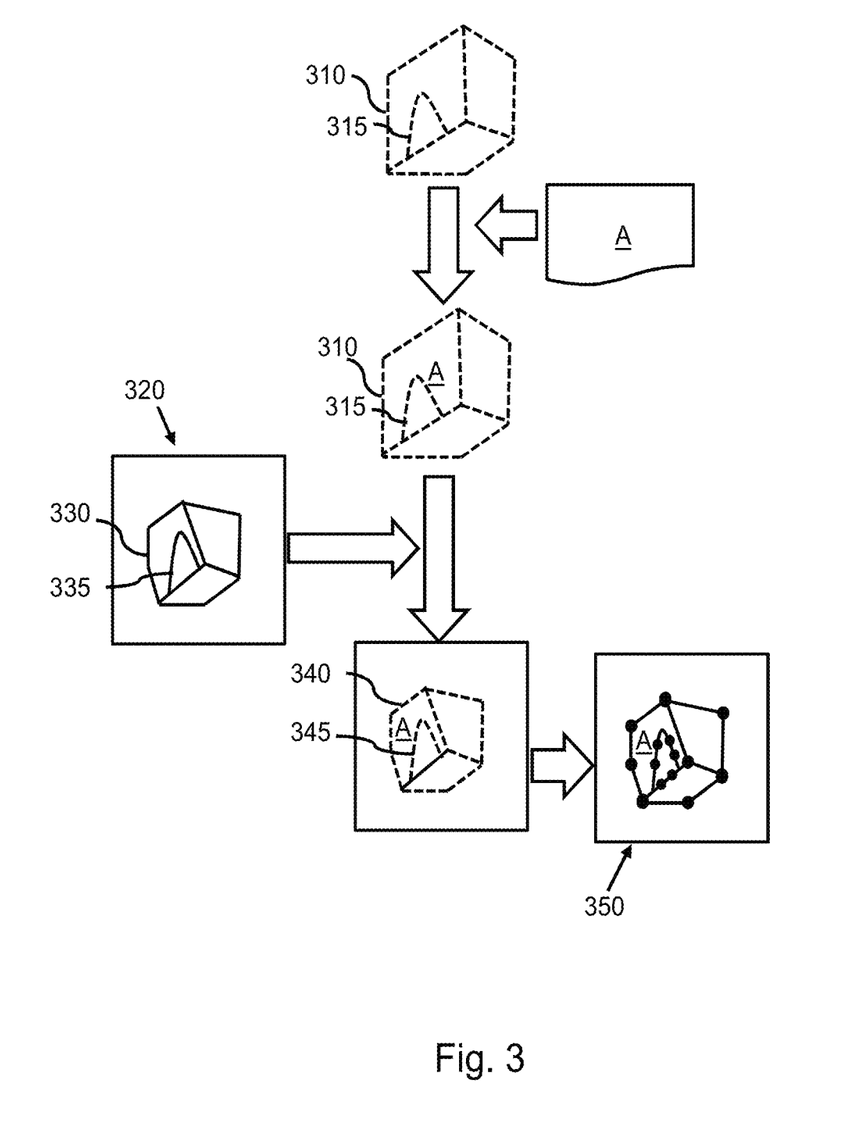
FIG. 3 schematically illustrates generating a finite element model of an anatomical structure based on a fitted model of the anatomical structure and association data.

FIG. 3 schematically illustrates an example of the first method of FIG. 2 for generating association data and an example of the second method of FIG. 2 for generating a finite element model 350 of an anatomical structure 330. In this example, first, model data defining a segmentation model 310 for segmenting an anatomical structure 330 may be obtained. In the example of FIG. 3, the segmentation model 310 is schematically indicated as a cube and the segmentation model part 315 of the segmentation model 310 representing the pre-determined anatomical region of interest is schematically indicated as an arc-shaped region. It will be appreciated that in practice, the pre-determined anatomical region of interest may be any anatomical region with a characteristic of interest, the latter being, e.g., a material type, a medical and/or biological condition, a mechanical boundary or anatomical shape. Likewise, the segmentation model 310 may be a model of any anatomical structure with various levels of anatomical complexity, e.g., heart model or a model representing orthopedic features such as femur. The pre-determined anatomical region of interest in the segmentation model may be subsequently identified. The association data may be generated associating the segmentation model part 315 of the segmentation model 310 with a mesh property e.g., a mesh resolution, the segmentation model part 315 representing a pre-determined anatomical region of interest. For example, if the segmentation model is a labeled model in that the model data comprises labels for different anatomical regions, the association data may be generated as to comprise or refer to the label of the segmentation model part 315, e.g., a label "A".

The segmentation model 310 may be applied to a medical image 320 of a subject, so as to fit the segmentation model 310 to the anatomical structure 330 in the medical image 320, thereby obtaining a fitted model 340 providing a segmentation of the anatomical structure 330, the fitted model 340 comprising a fitted model part 345 providing a segmentation of the pre-determined anatomical region of interest. As can be seen in FIG. 3, the fitted model better fits the anatomical structure.

It is noted that, in general, when applying the segmentation model 310 to the medical image 320 of the subject, so as to fit the segmentation model 310 to the anatomical structure 330 in the medical image 320, the segmentation model part 315 of the segmentation model 310 may be fitted to the pre-determined anatomical region of interest 335 in the medical image 320 so as to obtain the fitted model 340 comprising a fitted model part 345 providing a segmentation of the pre-determined anatomical region of interest.

It is also noted that, in general, when applying the segmentation model 310 to the medical image 320 of the subject, so as to fit the segmentation model 310 to the anatomical structure 330 in the medical image 320, the association data may associate the fitted model part 345 with the mesh property. As such, the association data may associate both the segmentation model part 315 of the segmentation model 310 and the fitted model part 345 of the fitted model 340 with the mesh property.

The finite element model 350 may be generated based on the fitted model 340 and the association data. The generation of the finite element model 350 may comprise meshing of a finite element model part of the finite element model in accordance with the mesh property, the finite element model part corresponding with the pre-determined anatomical region of interest.

It is noted that for achieving a desired mesh resolution associated with a region, for example, decimation methods may be applied within the region until the desired mesh is achieved. In a case of a tetrahedral mesh, for example, this may be done by taking all the four vertices of a tetrahedron, and by fusing them onto the barycenter, e.g., the geometric center of the tetrahedron as described in "Chopra, P.; Meyer, J., TetFusion: an algorithm for rapid tetrahedral mesh simplification," Visualization, 2002. VIS 2002. IEEE, vol., no., pp. 133,140, 1-1 Nov. 2002 doi: 10.1109/VISUAL.2002.1183767".

It is also noted that for encoding information representing a mesh property in a mesh model, e.g., a mesh resolution, an information propagation method may be used, e.g., the information may be encoded in mesh triangles of the segmentation mesh and the encoded information may be propagated into an enclosed volume, e.g. by defining a distance weighted average resulting in a volumetric mesh resolution map. Decimation may be performed until a locally desired mesh resolution is achieved. In this way, abrupt changes of volumetric mesh resolution differences that may result from decimation of separate connected regions may be avoided. In some cases, it may be useful to convert surfaces resulting from segmentation into volumetric layers. Information about a desired thickness of the layer may be encoded into respective surfaces. After segmentation, dilatation or front propagation techniques may be used to construct a layer of the desired thickness in a label image.

Figure 4A:
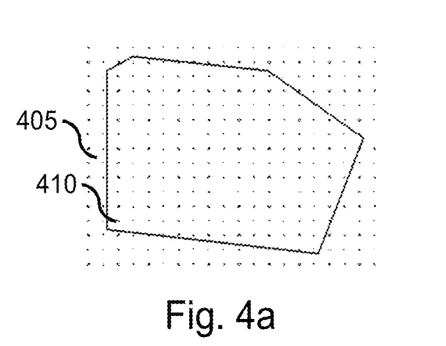
FIGS. 4a-f show an example of the meshing of an anatomical region of interest in a 2D anatomical structure.
Figure 4B:
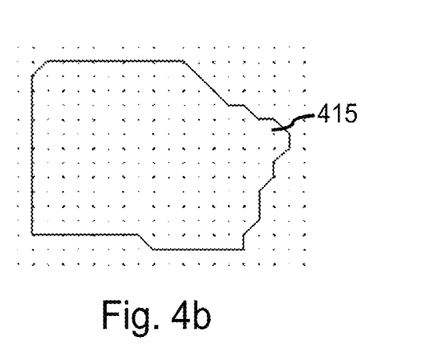
Figure 4C:
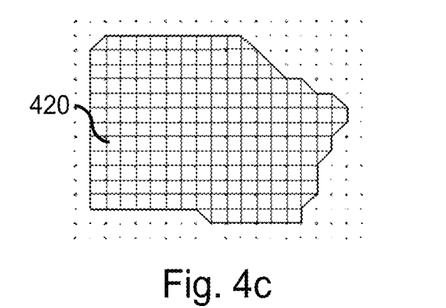
Figure 4D:
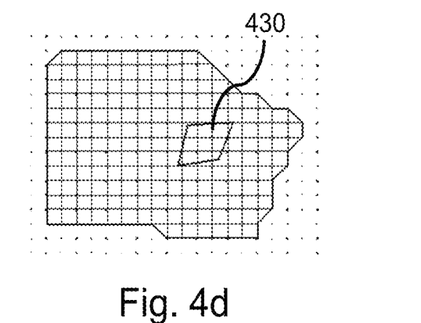
Figure 4E:
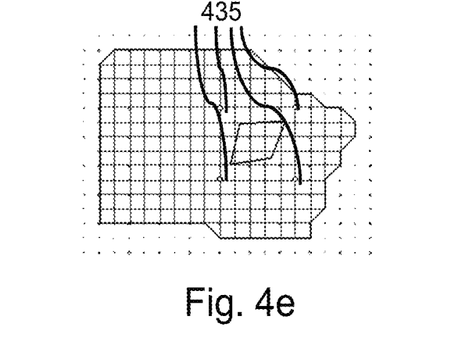
Figure 4F:
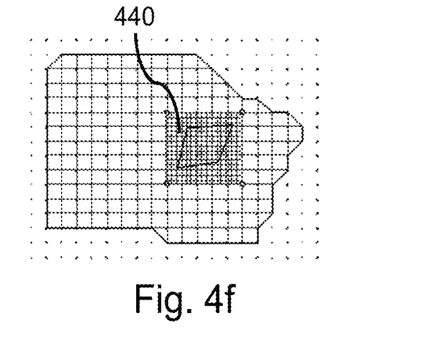

FIGS. 4a-f show an example of the meshing of a finite element model part 430 of a finite element model corresponding with a pre-determined anatomical region of interest in an anatomical structure 410 based on a particular mesh property indicating a high resolution for the finite element model part 430 in the anatomical structure 410. For the sake of ease of explanation, a 2D structure is shown to represent the anatomical structure 410. As shown in FIG. 4a, a regular array of grid points 405 may be created and the anatomical structure 410 may be overlaid on the regular array. The granularity of the regular array 405 may be ascertained from pre-sets or user input. External boundary 415 of the anatomical structure 410 may be modified to match points on the regular array 405, as shown in FIG. 4b. Horizontal and vertical lines may be then created between the points on the regular array 405 such that an internal grid 420 may be formed within the anatomical structure 410, as shown in FIG. 4c. The finite element model part 430 within the anatomical structure 410 may be identified, as shown in FIG. 4d. A set of co-ordinates 435, also referred to as bounding points, in the regular array 405 may be identified such that the set of co-ordinates 435 completely bound the finite element model part 430 and form a bound region 440, as shown in FIG. 4e. A space between the anatomical structure 410 and the bounding points may be set by pre-sets, by the user or information from a database. In this example, a set of grid points may be created within the bound region 440 to form a sub-grid, such that (i) sub-grid points may be equal divisions of the internal grid 420, (ii) a granularity of the sub-grid matches a specified mesh. A sub-array may be formed by connected the vertical and horizontal sub-grid points, as shown in FIG. 4f. As such, using the sub-grid, a mesh with a desired resolution may be generated in the finite element model part 430 in the anatomical structure 410.

Figure 5:
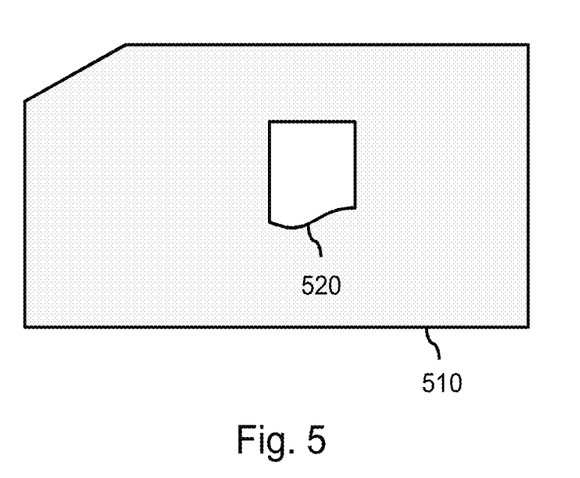
FIG. 5 shows a schematic representation model data and encoded association data for use in generating a finite element model of an anatomical structure.

FIG. 5 shows a schematic representation model data 510 and association data 520 for use in generating a finite element model of an anatomical structure. In the example of FIG. 5, the association data 520 is shown to be part of the model data 510. For example, the association data may be encoded in the model data, e.g., in a header or as one or more properties assigned to the pre-determined region of interest. It will be appreciated that the association data 520 may also be generated in separation of the model data 510, e.g., as metadata which can be associated with the model data 510.

Figure 6:
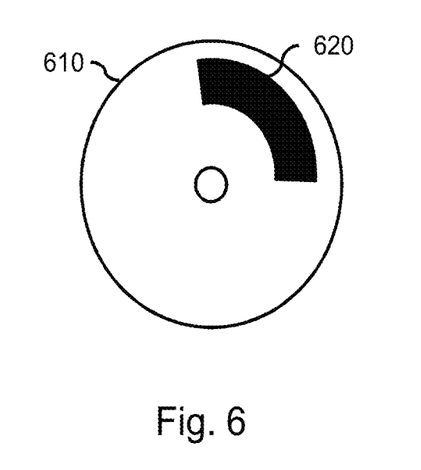
FIG. 6 shows a schematic representation of a computer program product comprising instructions for causing a processor system to perform the method for generating a finite element model of an anatomical structure based on a fitted model of the anatomical structure and association data and/or the method for generating the association data for use in generating the finite element model of the anatomical structure.

The methods 150 and 200 of FIG. 2 may be implemented on a computer as a computer implemented method, as dedicated hardware, or as a combination of both. As illustrated in FIG. 6, instructions for the computer, i.e., executable code, may be stored on a computer program product 610, e.g., in the form of a series 620 of machine readable physical marks and/or as a series of elements having different electrical, e.g., magnetic, or optical properties or values. The executable code may be stored in a transitory or non-transitory manner. Examples of computer program products include memory devices, optical storage devices 610, integrated circuits, servers, online software, etc. FIG. 6 shows an optical disc.

It is noted that artifacts in a medical image of an anatomical structure may be used for identifying a region of interest in the anatomical structure. Here, the term 'artifacts' may refer to medical artifacts, e.g., pathologies. For that purpose, an anatomical intelligence algorithms may be used which may apply one or more image analysis techniques to identify, e.g., a surface of the anatomical structure, artifacts, or features of interest within the anatomical structure. For example, the anatomical intelligence algorithm may be used in the identification subsystem of the provided device for identifying an anatomical region of interest in the medical image based on an identification of a region with a particular image intensity, indicating, e.g., an abnormal regional material property and thereby a pathology.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be subdivided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for generating association data for use in generating a finite element model of an anatomical structure, the system comprising:
   an input interface configured for obtaining model data defining a segmentation model for segmenting the anatomical structure, the segmentation model representing a reference shape of the anatomical structure;
   an identifying subsystem configured for identifying a pre-determined anatomical region of interest in the segmentation model, the pre-determined anatomical region of interest having been pre-determined based on a mesh property being desired in meshing a finite element model part of the finite element model which corresponds with the pre-determined anatomical region of interest;
   an association subsystem configured for generating association data associating a segmentation model part of the segmentation model with the mesh property, the segmentation model part representing the pre-determined anatomical region of interest;
   wherein the mesh property includes:
   (i) mesh resolution of the finite element part of the finite element model, and
   (ii) a type of finite element in the finite element part of the finite element model.

2. A method for generating associated data for use in generating a finite element model of an anatomical structure, comprising:
   obtaining model data defining a segmentation model for segmenting the anatomical structure, the segmentation model representing a reference shape of the anatomical structure;
   identifying a pre-determined anatomical region of interest in the segmentation model, the pre-determined anatomical region of interest having been pre-determined based on a mesh property being desired in meshing a finite element model part of the finite element model which corresponds with the pre-determined anatomical region of interest;
   generating association data associating a segmentation model part of the segmentation model with the mesh property, the segmentation model part representing the pre-determined anatomical region of interest;
   wherein the mesh property includes:
   (i) mesh resolution of the finite element part of the finite element model, and
   (ii) a type of finite element in the finite element part of the finite element model.

3. A non-transitory computer-readable medium comprising instructions that, in response to execution of the instructions by one or more processors, cause the one or more processors to perform the method of claim 2.

4. A system for generating association data for use in generating a finite element model of an anatomical structure, the system comprising:
   an input interface configured to receive model data defining a segmentation model for segmenting the anatomical structure, the segmentation model representing a reference shape of the anatomical structure; and
   one or more processors configured to perform the method of claim 2.

5. A system for generating association data for use in generating a finite element model of an anatomical structure, the system comprising:
   an input interface configured for receiving model data defining a segmentation model for segmenting the anatomical structure, the segmentation model representing a reference shape of the anatomical structure; and
   one or more processors configured to:
      obtain the model data received by the input interface,
      identify the anatomical region of interest based on mesh properties selected for meshing a part of the finite element model which corresponds with the anatomical region of interest,
      generate association data associating a segment model part of the segmentation model with the mesh property, wherein the part of the segmentation model represents the predetermined anatomical region of interest;

wherein the selected mesh properties include:
(i) mesh resolution of the finite element part of the finite element model, and
(ii) a type of finite element in the finite element part of the finite element model.

6. The system according to claim 5, wherein the mesh properties include a shape of a finite element in the part of the finite element model representing the predetermined anatomical region of interest.

\* \* \* \* \*